United States Patent [19]
Schefczik et al.

[11] Patent Number: 5,206,375
[45] Date of Patent: Apr. 27, 1993

[54] THIOPHENE DERIVATIVES

[75] Inventors: Ernst Schefczik, Ludwigshafen; Karl-Heinz Etzbach; Heinz Eilingsfeld, both of Frankenthal, all of Fed. Rep. of Germany

[73] Assignee: BASF Aktiengesellschaft, Ludwigshafen, Fed. Rep. of Germany

[21] Appl. No.: 865,685

[22] Filed: Apr. 8, 1992

Related U.S. Application Data

[63] Continuation of Ser. No. 512,583, Apr. 23, 1990, abandoned, which is a continuation of Ser. No. 385,951, Jul. 28, 1989, abandoned, which is a continuation of Ser. No. 282,856, Dec. 8, 1988, abandoned, which is a continuation of Ser. No. 833,281, Feb. 27, 1986, abandoned.

[30] Foreign Application Priority Data

Mar. 2, 1985 [DE] Fed. Rep. of Germany ....... 3507421
Oct. 2, 1985 [DE] Fed. Rep. of Germany ....... 3535134

[51] Int. Cl.$^5$ .................. C07D 277/60; C07D 277/62; C07D 263/52; C07D 333/38
[52] U.S. Cl. ..................... 548/152; 548/179; 548/217; 548/304.7; 549/61; 534/753; 8/662; 8/690; 8/691; 8/692
[58] Field of Search .................. 549/61; 548/527, 152, 548/179, 217, 327; 546/212; 544/146, 147, 379

[56] References Cited

U.S. PATENT DOCUMENTS

| | | | |
|---|---|---|---|
| 4,108,867 | 8/1978 | Baird et al. | 549/61 |
| 4,111,956 | 9/1978 | Baird et al. | 549/61 |

FOREIGN PATENT DOCUMENTS

| | | | |
|---|---|---|---|
| 2513337 | 10/1976 | Fed. Rep. of Germany | 549/61 |
| 59-204658 | 9/1983 | Japan . | |
| 0042376 | 3/1984 | Japan | 549/61 |
| 0190776 | 9/1985 | Japan | 549/61 |
| 60-208976 | 2/1986 | Japan . | |
| 1583377 | 1/1981 | United Kingdom . | |

OTHER PUBLICATIONS

Research Disclosure, Oct. 1980, ref. 19826, pp. 425–427, "Discharge/Resist Printing of Synthetic Textile Materials Using Thiophene-azo Disperse Dyestuffs in the Presence of Alkali".

Chemical Abstracts, Band 104, Nr. 3, 20. Jan. 1986, Seite 476, Nr. 1950f, Columbus, Ohio, US; & JP-A-60 161 978 (Mitsui Toatsu Chemicals Inc.) 23-08-1985, Zusammenfassung.

*Primary Examiner*—Alan Siegel
*Attorney, Agent, or Firm*—Oblon, Spivak, McClelland, Maier & Neustadt

[57] ABSTRACT

The novel compound of the general formula I

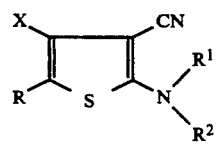

where X is fluorine, chlorine, bromine, $SO_2Y$ or unsubstituted or substituted hydroxyl or mercapto, Y is alkyl, alkenyl, cycloalkyl, aralkyl, aryl, chlorine or unsubstituted or substituted hydroxyl or amino, R is hydrogen, $C_1$–$C_4$-alkyl or a radical which can be introduced by electrophilic substitution or a radial of the formula —CH=T, in which T is a radical of a methyleneactive compound or of an amine, and $R^1$ is hydrogen, acyl or unsubstituted or substituted alkyl, cycloalkyl or alkenyl, and $R^2$ is hydrogen or unsubstituted or substituted alkyl or alkenyl, or $R^1$ and $R^2$ together with the nitrogen form a saturated heterocyclic structure and $R^1$ and $R^2$ together form a radical of the formula

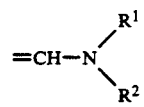

are useful as diazo and/or coupling components or generally as dye intermediates, depending on their constitution.

3 Claims, No Drawings

THIOPHENE DERIVATIVES

This application is a continuation of application Ser. No. 07/512,583, filed on Apr. 23, 1990, now abandoned, which is a continuation of application Ser. No. 385,951, filed on Jul. 28, 1989, now abandoned which is a continuation of application Ser. No. 07/282,856, filed on Dec. 8, 1988, now abandoned which is a continuation of application Ser. No. 06/833,281, filed On Feb. 27, 1986, now abandoned.

The present invention relates to compounds of the general formula I

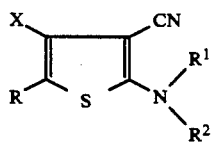

where X is fluorine, chlorine, bromine, $SO_2Y$ or unsubstituted or substituted hydroxyl or mercapto, Y is alkyl, alkenyl, cycloalkyl, aralkyl, aryl, chlorine or unsubstituted hydroxyl or amino, R is hydrogen, $C_1$-$C_4$-alkyl or a radical which can be introduced by electrophilic substitution or a radical of the formula —CH=T in which T is a radical of a methylene-active compound or of an amine, $R^1$ is hydrogen, acyl or unsubstituted or substituted alkyl, cycloalkyl or alkenyl and $R^2$ is hydrogen or unsubstituted or substituted alkyl or alkenyl, or $R^1$ and $R^2$ together with the nitrogen form a saturated heterocyclic structure and $R^1$ and $R^2$ together form a radical of the formula

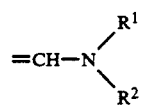

Examples of radicals X, in addition to those stated above, are alkoxy, cycloalkoxy, aralkoxy and aryloxy, as well as the corresponding mercapto radicals. Specific examples are OH, $OCH_3$, $OC_2H_5$, $OC_3H_7$, $OC_4H_9$, $OCH_2C_6H_5$, $OC_6H_{11}$, $OC_6H_5$, $OC_6H_4CH_3$, $OC_6H_4Cl$, SH, $SCH_3$, $SC_2H_5$, $SC_3H_7$, $S_4H_9$, $SCH_2C_6H_5$, $SC_2H_4OH$, $SCH_2COOCH_3$, $SCH_2COOC_2H_5$, $SC_6H_{11}$, $SC_6H_5$ and $SC_5H_4CH_3$ Y is, for example, $CH_3$, $C_2H_5$, $C_3H_7$, $C_4H_9$, $C_6H_{13}$, $C_6H_{11}$, $C_8H_{17}$, $C_6H_5$—$CH_2$, $C_6H_5$—$CH_2$—$CH_2$, $C_6H_5$, Cl—$C_6H_4$, $C_4H_9$—$C_6H_4$, Cl, OH, $CH_3O$, $C_2H_5O$, $C_3H_7O$, $C_4H_9O$, $C_6H_5$—$CH_2O$, $C_6H_5$-$CH_2$-$CH_2O$, $C_6H_5O$, $ClC_6H_4O$, $CH_3C_6H_4O$, $NH_2$, $NHCH_3$, $N(CH_3)_2$, $NHC_2H_5$, $N(C_2H_5)_2$, $NHC_4H_9$, $N(C_4H_9)_2$, $NHC_6H_5$, $NHC_6H_4$—$CH_3$, $NHC_6H_4Cl$ and $NCH_3C_6H_4$.

Examples of radicals R which can be introduced electrophilically are Cl, Br, NO, $NO_2$, $SO_3H$, CHO, CN and acyl radicals, eg. $CH_3CO$, $C_2H_5CO$, $C_6H_5CO$, $CH_3SO_2$, $C_2H_5SO_2$ or $C_6H_5SO_2$.

Methylene-active compounds of the formula $H_2T$ are, for example, compounds of the formula

where Z is cyano, nitro, alkanoyl, aroyl, alkylsulfonyl, arylsulfonyl, carboxyl, a carboxylic ester group or unsubstituted or substituted carbamyl, and the compounds of the formulae:

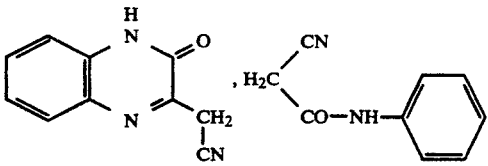

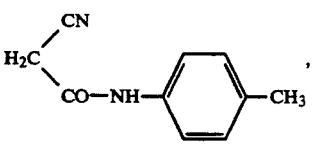

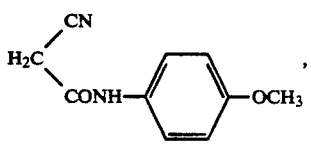

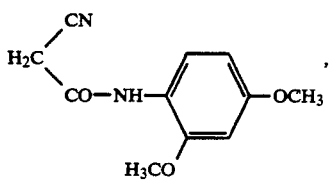

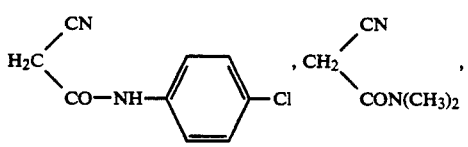

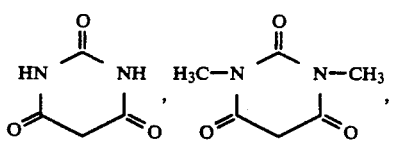

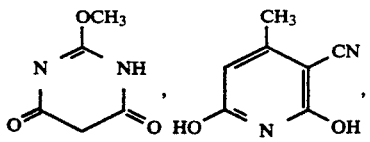

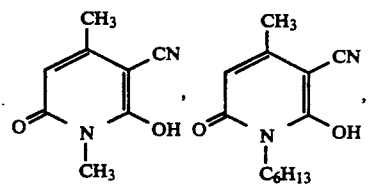

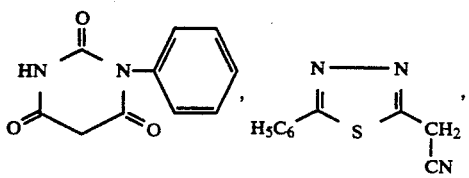

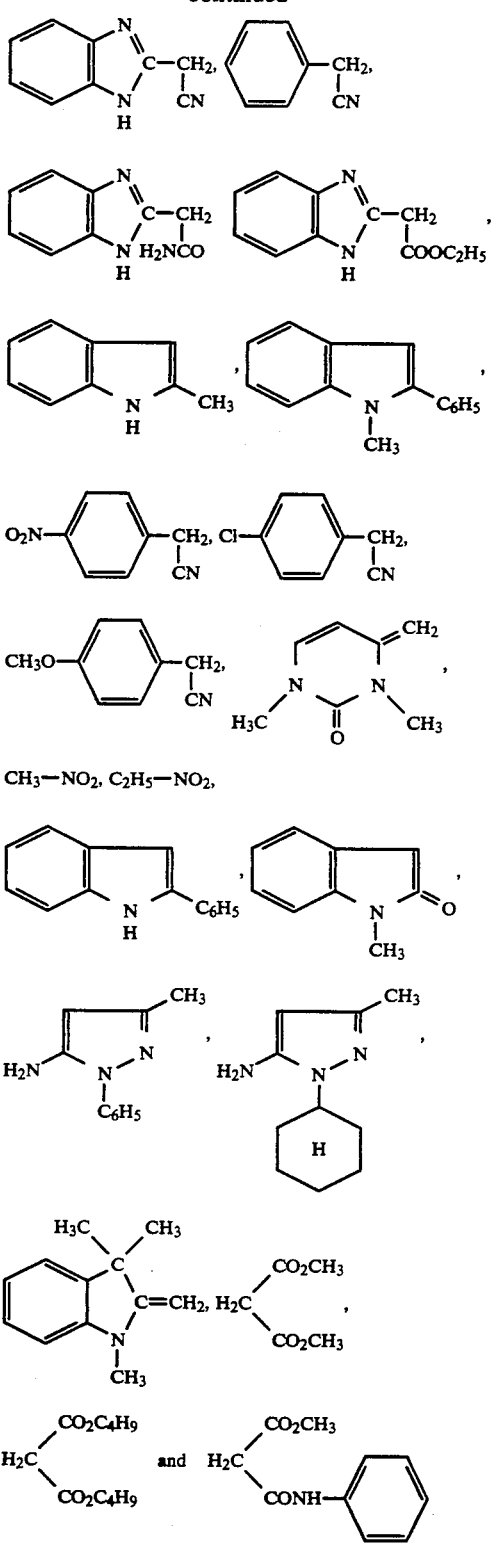

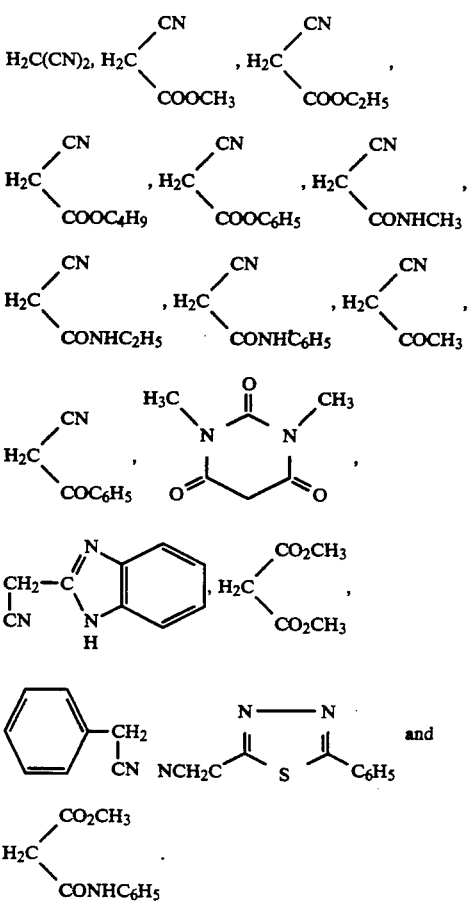

Specific examples of important compounds of the formula

are:

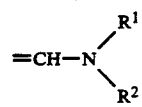

Amine radicals T are, for example, =N—C$_6$H$_5$, =N—C$_6$H$_4$CH$_3$ or general radicals of Schiff's bases of the amines.

Alkyl radicals R are, for example CH$_3$, C$_2$H$_5$, C$_3$H$_7$ or C$_4$H$_9$.

In conformity with the general definition, examples of radicals R$^1$ and R$^2$, in addition to hydrogen, C$_1$–C$_4$-alkyl which is unsubstituted or substituted by chlorine, bromine, cyano, hydroxyl, C$_1$–C$_4$-alkoxy, C$_1$–C$_8$-alkanoyloxy, C$_1$–C$_8$-alkoxycarbonyl, phenyl or tolyl, or are C$_3$–C$_5$-alkenyl or C$_5$–C$_7$-cycloalkyl.

Specific examples are CH$_3$, C$_2$H$_5$, C$_3$H$_7$, C$_4$H$_9$, C$_2$H$_4$OH, CH$_2$CHOHCH$_3$, C$_2$H$_4$CN, C$_2$H$_4$OCH$_3$, C$_2$H$_4$OC$_2$H$_5$, C$_2$H$_4$OC$_4$H$_9$, C$_2$H$_4$OCOCH$_3$, C$_2$H$_4$OCOC$_2$H$_5$, C$_2$H$_4$OCOC$_8$H$_{17}$, C$_2$H$_4$COOCH$_3$, C$_2$H$_4$COOC$_2$H$_5$, C$_2$H$_4$COOC$_4$H$_9$, C$_2$H$_4$COOC$_8$H$_{17}$, CH$_2$C$_6$H$_5$, C$_2$H$_4$C$_6$H$_5$, CH$_2$C$_6$H$_4$CH$_3$, C$_2$H$_4$C$_6$H$_4$CH$_3$, cyclohexyl, cycloheptyl, allyl and methallyl.

R$^1$ and R$^2$ together with the nitrogen are, for example, pyrrolidino, piperidino, morpholino, piperazino or N-methylpiperazino.

Radicals of the formula $$=CH-N\begin{matrix}R^1\\R^2\end{matrix}$$

are preferably =CH—N(CH$_3$)$_2$, =CH—N(C$_2$H$_5$)$_2$ or

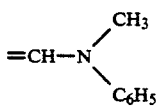

Compounds of the formula I where R is H or $C_1$–$C_4$-alkyl can be prepared by reacting a compounds of the formula II

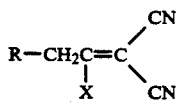

with a sulfur donor. Radicals R can be introduced into the compounds of the formula I in which R is H by electrophilic substitution by a conventional method.

Furthermore, the compound of the formula I where R is H and X is OH may be prepared by reacting the compound of the formula

with malodinitrile and then reacting the product with a sulfide.

The Examples which follow illustrate the preparation. Parts and percentages are by weight, unless stated otherwise.

Japanese Preliminary Published Application 84/42376 of Nippon Kayaku Co. states that reacting mercaptoacetates with malodinitrile would give compounds of the formula I. However, as is clear from J. Org. Chem. 38 (1973), 3616 and J. Heterocyclic Chem. 16 (1979), 1541, this is not the case since these reactions give exclusively thiazole derivatives.

Where R is H, the compounds of the formula I are useful both as diazo components and as coupling components.

Particularly important diazo components are compounds of the formula Ia

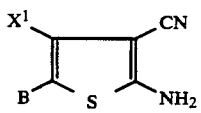

where $X^1$ is chlorine, hydroxyl, $C_1$–$C_4$-alkoxy, $C_1$–$C_4$-alkylthio, methylsulfonyl, phenylsulfonyl, hydroxysulfonyl, phenoxy or phenylthio and B is hydrogen, $C_1$–$C_4$-alkyl, formyl, acetyl, nitro, hydroxysulfonyl or cyano.

Particularly useful coupling components are compounds of the formula Ib

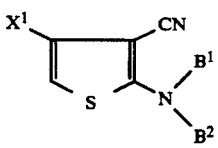

where $B^1$ is hydrogen, $C_1$–$C_4$-alkyl, $C_2$- or $C_3$-hydroxyalkyl, cyanoethyl, $C_1$–$C_4$-alkoxycarbonylethyl, $C_1$–$C_4$-alkanoyloxyethyl, allyl, benzyl, phenylethyl or cyclohexyl, $B^2$ is hydrogen, $C_1$–$C_4$-alkyl, $C_2$- or $C_3$-hydroxyalkyl, cyanoethyl, $C_1$–$C_4$-alkoxycarbonylethyl, $C_1$–$C_4$-alkanoyloxyethyl or allyl and $X^1$ has the meanings stated for formula Ia.

EXAMPLES

Example 1

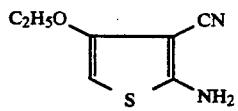

136 parts of 2-cyano-3-ethoxycrotononitrile are dissolved in 200 parts of N-methylpyrrolidone, and 32 parts of flowers of sulfur are added. 25 parts of triethylamine are then poured in, the reaction mixture warming up and the initially suspended sulfur going into solution. When the temperature reaches 50° C., the mixture is cooled by means of a water bath, and the temperature kept at 40°–50° C. After 2 hours, 1000 parts of water are added to the clear solution, the product being precipitated in crystalline form. It is filtered off under suction, washed with water and dried at 60° C. under reduced pressure. 142 parts of 2-amino-3-cyano-4-ethoxythiophene are obtained in the form of slightly brownish crystals which darken substantially on storage. A sample recrystallized from toluene has a melting point of 145°–146° C. and the following analytical values:

| $C_7H_8N_2OS$ (168) | | | | | |
|---|---|---|---|---|---|
| calculated: | C 50.0 | H 4.8 | N 16.7 | O 9.5 | S 19.0 |
| found: | 50.0 | 4.9 | 16.8 | 9.8 | 18.9 |

IR and NMR spectra confirm the constitution.

Example 2

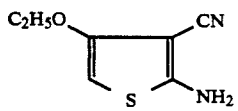

600 parts of dimethylformamide, 40 parts of triethylamine and 128 parts of flowers of sulfur are stirred at room temperature. 544 parts of 2-cyano-3-ethoxycrotononitrile are then added a little at a time at a rate such that the temperature of the reaction mixture remains at 40°–45° C. without heating. When the addition is complete, stirring is continued for 4 hours, after which 4000 parts of water are added. The suspension of crystals is rendered neutral by adding acetic acid and is worked up as described in Example 1.

623 parts (92.7% of theory) of 2-amino-3-cyano-4-ethoxythiophene are obtained.

Example 3

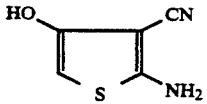

A solution of 20 parts by volume of concentrated hydrochloric acid in 100 parts by volume of water is added dropwise to a boiling mixture of 168 parts of 2-amino-3-cyano-4-ethoxythiophene and 500 parts by volume of methanol. The mixture is refluxed for a further 2 hours and diluted with 400 parts by volume of water, and the product is filtered off under suction, washed with water and dried to give 136 parts of 2-amino-3-cyano-4-hydroxythiophene. The sample recrystallized from acetic acid does not melt below 300° C. and has the following analytical values:

| | C₅H₄N₂OS (140) | | | | |
|---|---|---|---|---|---|
| calculated: | C 42.9 | H 2.9 | N 20.0 | O 11.4 | S 22.9 |
| found: | 43.0 | 3.0 | 19.7 | 11.8 | 22.5 |

According to the IR spectrum, the product is identical to the compound prepared in Example 4.

Example 4

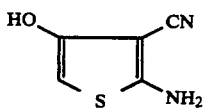

350 parts of triethylamine are added dropwise to a mixture of 178 parts of chloroacetyl chloride, 104 parts of malonodinitrile and 900 parts of dimethylformamide, while cooling with ice. The solution is stirred for a further hour at room temperature, after which it is introduced into a mixture of 294.5 parts of a 40% strength aqueous ammonium sulfide solution, 1000 parts of ice and 1000 parts of water, and the reaction mixture is stirred for a further 3 hours at room temperature. The precipitate formed is filtered off under suction, washed with water and dried. 137 parts (62% of theory) of 2-amino-3-cyano-4-hydroxythiophene are obtained.

Mp.:>300° C. (from glacial acetic acid); IR (KBr): 3260, 3061 (NH₂), 2219 (C≡N), 1668, 1641 cm⁻¹ (C=O).

Example 5

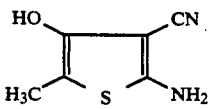

194 parts of triethyl orthopropionate and 66 parts of malodinitrile are stirred for 1 hour at 100° C. under a descending condenser. To remove volatile constituents, the mixture is kept under reduced pressure for 30 minutes and then left to cool. The mixture is taken up in 150 parts by volume of dimethylformamide, and 32 parts of flowers of sulfur are added. Thereafter, 100 parts by volume of triethylamine are added dropwise, the temperature being kept at <60° C. by cooling. Stirring is continued for a further 2 hours at 50° C., 500 parts of water and 150 parts of concentrated hydrochloric acid are added and the mixture is boiled for 1 hour and then cooled, after which the product is filtered off under suction, washed with water and dried. 131 parts of 2-amino-3-cyano-4-hydroxy-5-methylthiophene are obtained. The compound is soluble in an alkaline medium, and a sample recrystallized from pentanol melts at 275'-276° C. and has the following analytical values:

| | C₆H₈N₂OS (154) | | | | |
|---|---|---|---|---|---|
| calculated: | C 46.8 | H 3.9 | N 18.2 | O 10.4 | S 20.8 |
| found: | 47.0 | 4.2 | 17.9 | 10.3 | 20.5 |

Example 6

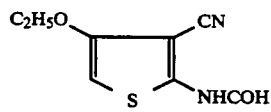

200 parts of formic acid are added dropwise to 500 parts of acetic anhydride at room temperature, and 168 parts of 2-amino-3-cyano-4-ethoxythiophene are introduced after 2 hours. The mixture is stirred for 4 hours at 50° C., after which 1000 parts of water are run into the hot mixture. The mixture is cooled and the product is then filtered off under suction, washed with water and dried. 174 parts of 2-formylamino-3-cyano-4-ethoxythiophene of melting point 191°-192° C. (from pentanol) are obtained.

Example 7

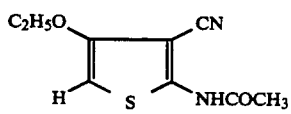

100 parts of anhydrous sodium acetate are introduced into 400 parts by volume of acetic anhydrice, 168 parts of 2-amino-3-cyano-4-ethoxythiophene are added and the mixture is refluxed for 4 hours. Thereafter, 800 parts of water are added dropwise to the hot mixture, the mixture is left to cool and the product is filtered off under suction, washed with water and dried to give 194 parts of 2-acetylamino-3-cyano-4-ethoxythiophene of melting point 242°-243° C. (from acetic acid).

| | C₉H₁₀N₂O₂S (210) | | | | |
|---|---|---|---|---|---|
| calculated: | C 51.4 | H 4.8 | N 13.3 | O 15.2 | S 15.3 |
| found: | 51.2 | 4.7 | 13.3 | 15.5 | 15.2 |

2-Propionylamino-3-cyano-4-ethoxythiophene is prepared by a similar method and has a melting point of 223°-224° C. (from pentanol).

Example 8

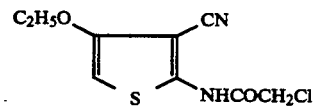

168 parts of 2-amino-3-amino-4-ethoxythiophene are dissolved in 500 parts by volume of dimethylformamide, 101 parts of triethylamine are added, and 130 parts of monochloroacetyl chloride are introduced dropwise at 50° C. Stirring is continued for 4 hours at 50° C., after which the reaction mixture is poured onto 2000 parts of water. The product is filtered off under suction, washed with water and dried, and 240 parts of 2-(2-chloroacetylamino)-3-cyano-4-ethoxythiophene are obtained. A sample recrystallized from acetic acid melts at 243°-244° C. and has a chlorine content of 14.1% (calculated: 14.5%).

Example 9

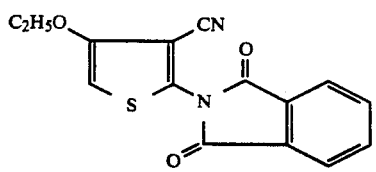

90 parts of anhydrous sodium acetate and 160 parts of phthalic anhydride are dissolved in 1000 parts of acetic acid, 168 parts of 2-amino-3-cyano-4-ethoxythiophene are added and the mixture is refluxed for 6 hours. It is diluted with 500 parts of water and left to cool, and the product is filtered off under suction, washed with water and dried to give 203 parts of 2-phthaloylimino-3-cyano-4-ethoxythiophene of melting point 173°-174° C. (from acetic acid).

Example 10

350 parts of phosphoryl trichloride are added dropwise to a solution of 200 parts of dimethylformamide in 2000 parts by volume of toluene at 10°-20° C. while cooling. Thereafter, 168 parts of 2-amino-3-cyano-4-ethoxythiophene are introduced and the mixture is stirred for 8 hours at 40° C. After the mixture has cooled, the precipitated crystals are filtered off under suction, washed with ethyl acetate and dried under reduced pressure at 30° C. 271 parts of a compound having the constitution

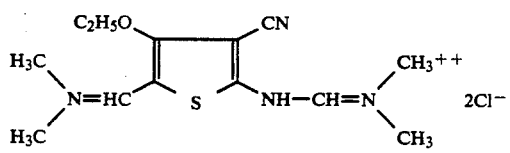

a Cl⊖ content of 19.9% (calculated: 20.2%) and a melting point of 159°-160° C. are obtained.

Example 11

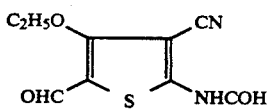

400 parts of phosphoryl trichloride are added dropwise to a mixture of 1500 parts by volume of chloroform and 250 parts of dimethylformamide, while cooling with ice, after which 168 parts of 2-amino-3-cyano-4-ethoxythiophene are added and the mixture is refluxed for 4 hours. As the mixture cools, colorless crystals are precipitated. The mixture is diluted with 500 parts by volume of ethyl acetate, and the crystals are filtered off under suction and washed with ethyl acetate. The crystal cake is introduced into 2000 parts of ice water, and brought to pH 8 by stirring with sodium hydroxide Solution. After 4 hours, the product is filtered off under suction, washed with water and dried. 176 parts of 2-formylamino-3-cyano-4-ethoxy-5-formylthiophene are obtained. A sample recrystallized from pentanol melts at 230°-231° C. and has the following analytical values:

| | $C_9H_8N_2O_3S$ (224) | | | | |
|---|---|---|---|---|---|
| calculated: | C 48.2 | H 3.6 | N 12.5 | O 21.4 | S 14.3 |
| found: | 48.3 | 3.9 | 12.7 | 21.1 | 14.5 |

Example 12

224 parts of 1-formylamino-2-cyano-3-ethoxy-4-formylthiophene and 120 parts of hydroxylammonium chloride are introduced into 2000 parts by volume of methanol, and the mixture is stirred at room temperature. A solution of 80 parts of sodium acetate in 300 parts of water is poured in, and the mixture is refluxed for 6 hours. After the mixture has cooled, it is diluted with 1000 parts of water and the product is filtered off under suction and dried to give 232 parts of a compound having the constitution

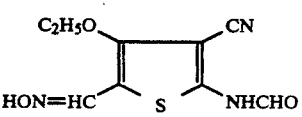

in the form of colorless crystals. A sample recrystallized from pentanol melts at 255°-256° C. and has the following analytical values:

| | $C_9H_9N_3O_3S$ (239) | | | | |
|---|---|---|---|---|---|
| calculated: | C 45.2 | H 3.8 | N 17.6 | O 20.1 | S 13.4 |
| found: | 45.2 | 3.7 | 17.4 | 20.1 | 13.3 |

Example 13

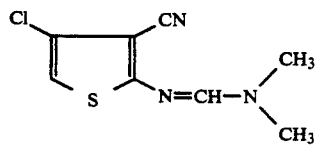

87.2 parts of phosphoryl trichloride are added dropwise to 600 parts of dimethylformamide while cooling with ice. The mixture is stirred for 0.5 hour at 5°-10° C., after which 66.5 parts of 2-amino-3-cyano-4-hydroxythiophene are added and the solution is heated for 1 hour at 70° C. Thereafter, the reaction mixture is introduced into 2000 parts of ice water, the mixture is filtered and 350 parts of sodium acetate are added to the stirred filtrate. The product then precipitated is filtered off under suction, washed with water and dried. 69.8 parts (69% of theory) of N-N-dimethyl-N'-(4-chloro-3-cyanothieny-2-yl)-formamidine are obtained.

Mp.: 67° C. (from toluene/hexane); IR (KBr): 3090 (CH), 2222 (C≡N), 1636 cm⁻¹ (C═N).

Example 14

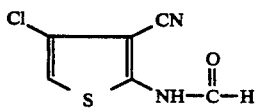

4.5 parts of N,N-dimethyl-N'-(4-chloro-3-cyano-thien-2-yl)-formamidine in a mixture of 20 parts of formic acid and 20 parts of water are heated at the boil for 1 hour. After the mixture has cooled to room temperature, the product is filtered off under suction, washed with water and dried. 3 parts (77% of theory) of N-(4-chloro-3-cyanothien-2-yl)-formamide are obtained.

Mp.: 241° C., IR (KBr): 2222 (C≡N), 1678, 1646 cm⁻¹ (C=O).

Example 15

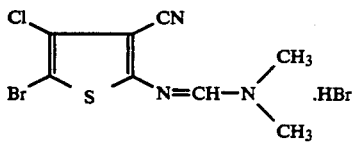

10.7 parts of N,N-dimethyl-N'-(4-chloro-3-cyano-thien-2-yl)-formamidine are dissolved in 100 parts of glacial acetic acid, after which 8 parts of bromine are added dropwise to the solution, and the mixture is then heated at the boil for 3 hours. After the mixture has cooled to room temperature, the resulting precipitate is filtered off under suction, washed with glacial acetic acid, then with aqueous sodium bisulfite solution and then with water and is dried. 13.4 parts (72% of theory) of N,N-dimethyl-N'-(5-bromo-4-chloro-3-cyanothien-2-yl)-formamidine hydrobromide are obtained.

Decomposition temperature: 223° C., IR (KBr): 2220 (C≡N), 1692, 1633 cm⁻¹ (C=N).

Example 16

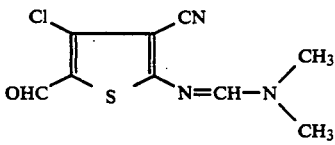

191 parts of phosphoryl trichloride are added dropwise to 700 parts of dimethylformamide, while cooling with ice, the mixture is stirred for a further 0.5 hour at 5°-10° C. and 70 parts of 2-amino-3-cyano-4-hydroxy-thiophene are then introduced. The solution is stirred for a further hour at 70° C., after which it is poured into 2000 parts of water. The precipitate formed is filtered off under suction, washed with water and dried. 116 parts (96% of theory) of N,N-dimethyl-N'-(4-chloro-3-cyano-5-formylthien-2-yl)-formamidine are obtained.

Mp.: 186° C. (from toluene), IR (KBr): 2220 (C≡N), 1657, 1623 cm⁻¹ (C=O, C=N).

Example 17

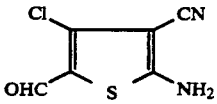

48.3 parts of N,N-dimethyl-N'-(4-chloro-3-cyano-5-formylthien-2-yl)-formamidine in a mixture of 200 parts of formic acid and 200 parts of water are heated at the boil for 3 hours. After the mixture has cooled to room temperature, the product is filtered off under suction, washed with water and dried. 33.5 parts (90% of theory) of 2-amino-4-chloro-3-cyano-5-formylthiophene are obtained. Decomposition temperature: 270° C. (from glacial acetic acid), IR (KBr): 3377, 3298, 3156 (NH₂), 2216 (C≡N), 1623 cm⁻¹ (C=O).

Example 18

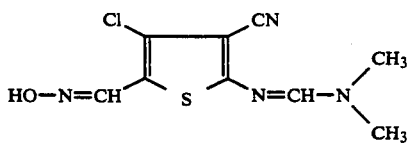

A stirred mixture of 9.7 parts of N,N-dimethyl-N'-(4-chloro-3-cyano-5-formylthien-2-yl)-formamidine, 2.8 parts of hydroxylamine hydrochloride, 3.3 parts of sodium acetate and 50 parts of dimethylformamide are heated at 50° C. for 3 hours, after which the solution is poured into 200 parts of water, and the precipitate is filtered off under suction and dried. 8.5 parts (83% of theory) of N,N-dimethyl-N'-(4-chloro-3-cyano-5-(N-hydroxyformimidyl)-thienyl-2-yl)-formamidine are obtained. Mp.: 199° C. (from glacial acetic acid), IR (KBr): 2220 (C≡N), 1639 cm⁻¹ (C≡N).

Example 19

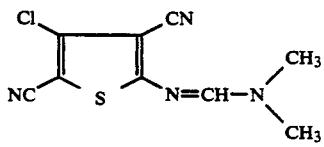

4.6 parts of phosphoryl trichloride are added to 70 parts of dimethylformamide, while cooling with ice, after which the mixture is stirred for a further 0.5 hour at 5°-10° C. and 7.7 parts of N,N-dimethyl-N'-(4-chloro-3-cyano-5-(N-hydroxyformimidyl)-thien-2-yl)-formamidine are then introduced. The solution is stirred for a further hour at room temperature, after which it is poured into 200 parts of water, and the resulting precipitate is filtered off under suction, washed with water and dried. 6.1 parts (85% of theory) of N,N-dimethyl-N'-(4-chloro-3,5-dicyanothien-2-yl)-formamidine are obtained. Mp.: 226° C. (from glacial acetic acid), IR (KBr): 2235, 2225 (C≡N), 1628 cm⁻¹ (C≡N).

Example 20

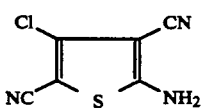

A mixture of 5.4 parts of N,N-dimethyl-N'-(4-chloro-3,5-dicyanothien-2-yl)-formamidine, 40 parts of ethanol and 4.5 parts of concentrated hydrochloric acid is heated at the boil for 2 hours and filtered while hot, and the filtrate is poured into 100 parts of water. The precipitate which separates out is filtered off under suction, washed with water and dried. 3.8 g (92% of theory) of 2-amino-4-chloro-3,5-dicyanothiophene are obtained.

Mp.: 259° C. (from glacial acetic acid), IR (KBr): 3435, 3334, 3206 (NH₂), 2210 cm⁻¹ (C≡N).

Example 21

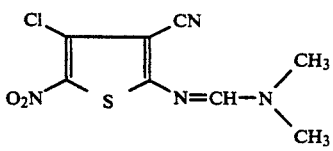

21.3 parts of N,N-dimethyl-N'-(4-chloro-3-cyano-thien-2-yl)-formamidine are introduced into 100 parts of 100% strength nitric acid, while cooling with ice. The mixture is stirred for 1 hour at room temperature, after which the product is precipitated by pouring the mixture onto ice water, and the precipitate formed is filtered off under suction, washed with water and dried to give 18.8 parts (73% of theory) of N,N-dimethyl-N'-(4-chloro-3-cyano-5-nitrothien-2-yl)-formamidine. Decomposition temperature: 254° C. (from glacial acetic acid).

Example 22

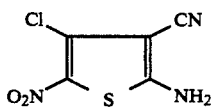

A mixture of 5.2 parts of N,N-dimethyl-N'-(4-chloro-3-cyano-5-nitrothien-2-yl)-formamidine, 50 parts of ethanol and 5 parts of concentrated hydrochloric acid is heated at the boil for 3 hours and then poured onto ice water. The precipitate is filtered off under suction, washed with water and dried. 3.2 parts (79% of theory) of 2-amino-4-chloro-3-cyano-5-nitrothiophene are obtained. Decomposition temperature: 227° C. (from o-dichlorobenzene).

Example 23

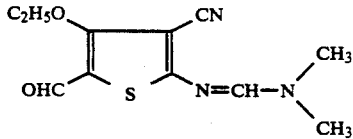

200 parts of phosphoryl trichloride are added dropwise to 700 parts of dimethylformamide, while cooling with ice. 168 parts of 2-amino-3-cyano-4-ethoxythiophene (Example 1) are then run in, and the mixture is stirred for a further 4 hours at 40° C. Thereafter, 100 parts of methanol are added dropwise, and 200 parts of anhydrous sodium acetate are introduced. The reaction mixture is then stirred with 1000 parts of ice, and 300 parts of 50% strength sodium hydroxide solution are added dropwise. Stirring is continued overnight, and the product is filtered off under suction, washed with water and dried to give 181 parts of the compound having the stated constitution and a melting point of 132°–133° C.

| $C_{11}H_{13}N_3O_2S$ (251) | | | | | |
|---|---|---|---|---|---|
| calculated: | C 52.6 | H 5.2 | N 16.7 | O 12.8 | S 12.8 |
| found: | 52.7 | 5.3 | 16.7 | 12.9 | 12.5 |

Example 24

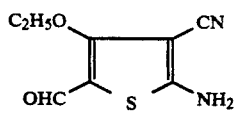

168 parts of 2-amino-3-cyano-4-ethoxythiophene (Example 1) are dissolved in 500 parts of dimethylformamide, and 200 parts of phosphoryl trichloride are added dropwise to the stirred solution. The reaction is exothermic, and the rate of dropwise addition is adjusted so that the temperature of the reaction mixture does not exceed 50° C. Stirring is continued for 4 hours at 50° C., 50 parts of ice are added, and the mixture is stirred until a clear solution has formed. This solution is run into 2000 parts of 12.5% strength sodium hydroxide solution and the temperature is kept at 20°–30° C. Stirring is continued for 8 hours at room temperature, after which the product is filtered off under suction, washed with water and dried. 185 parts of 2-amino-3-cyano-4-ethoxy-5-formylthiophene are obtained. A sample recrystallized from pentanol melts at 245°–246° C. and has the following analytical values:

| $C_8H_8N_2O_2S$ (196) | | | | | |
|---|---|---|---|---|---|
| calculated: | C 49.0 | H 4.1 | N 14.3 | O 16.3 | S 16.3 |
| found: | 49.2 | 4.2 | 14.3 | 16.6 | 15.9 |

Example 25

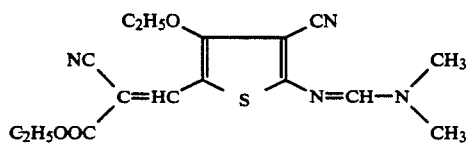

168 parts of 2-amino-3-cyano-4-ethoxythiophene (Example 1) are dissolved in 750 parts of dimethylformamide, and 200 parts of phosphoryl trichloride are added at 20°–30° C., while cooling. After stirring has been continued for 8 hours, a mixture of 120 parts of ethyl cyanoacetate and 250 parts of absolute ethanol is added dropwise, and 400 parts of anhydrous sodium acetate are then introduced. Stirring is continued overnight at room temperature, after which the mixture is diluted with 1500 parts of water. The product is filtered off under suction, washed with water and dried to give 294 parts of the compound of the above formula in the form of brown crystals. A sample recrystallized from ethanol melts at 153°–154° C. and has the following analytical values:

| $C_{16}H_{18}N_4O_3S$ (346) | | | | | |
|---|---|---|---|---|---|
| calculated: | C 55.4 | H 5.2 | N 16.2 | O 13.9 | S 9.4 |
| found: | 55.1 | 5.2 | 16.1 | 14.0 | 9.4 |

If the ethyl cyanoacetate is replaced with equivalent amounts of the methylene compounds

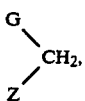

the same procedure gives the following compounds:

| G | Z | | Mp. |
|---|---|---|---|
| —CN | —CN | brown crystals | 221–222° (dimethyl-formamide) |
| —CN | —COOC4H9 | yellowish-brown crystals | 126–127° (toluene) |
| —CN | ![indoline] | orange red crystals | >350° (dimethyl-formamide) |
| ![barbiturate] | | yellowish-brown crystals | 293–294° (dimethyl-formamide) |
| ![dihydropyridine] | | reddish-violet crystals | 275–276° (dimethyl-formamide) |
| ![pyrazolone-SO3H] | | orange red, soluble in water | >350° |

Example 26

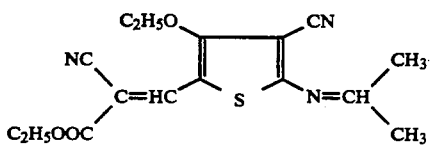

115 parts of ethyl cyanoacetate and 251 parts of the compound obtained as described in Example 23 are introduced into 1500 parts of anhydrous ethanol, and the mixture is then refluxed for 2 hours. After it has cooled, the product is filtered off under suction and dried at 50° C. to give 278 parts of brown crystals. The compound is identical to that obtained as described in Example 25.

Example 27

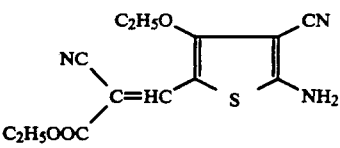

346 parts of the compound obtained as described in Example 26 are introduced into a mixture of 500 parts of N-methylpyrrolidone, 500 parts of water and 200 parts of concentrated hydrochloric acid, and the mixture is stirred for 4 hours at 100° C. Thereafter, a further 500 parts of water are added, the mixture is left to cool and the product is filtered off under suction, washed with water and dried to give 284 parts of a yellow compound of melting point 222°–223° C. (from acetic acid).

| | $C_{13}H_{13}N_3O_3S$ (291) | | | | |
|---|---|---|---|---|---|
| calculated: | C 53.6 | H 4.5 | N 14.4 | O 16.5 | S 11.0 |
| found: | 54.0 | 4.8 | 14.0 | 16.5 | 10.7 |

Example 28

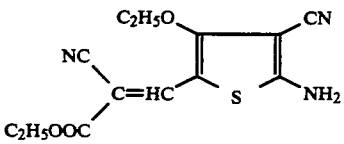

196 parts of 2-amino-3-cyano-4-ethoxy-5-formyl-thiophene (Example 24) and 125 parts of ethyl cyanoacetate are dissolved in 800 parts of N-methylpyrrolidone, and 20 parts of a saturated aqueous sodium acetate solution are added. The mixture is stirred for 12 hours at 25° C. and then diluted with 2000 parts of water. The product is filtered off under suction and dried to give 259 parts of a compound which is shown by IR spectra to be identical to the compound prepared as described in Example 27.

EXAMPLE 29

210 parts of 2-acetylamino-3-cyano-4-ethoxythiophene (Example 7) are introduced into 1000 parts of dimethylformamide, and 200 parts of phosphoryl trichloride are added dropwise in the course of 4 hours. Stirring is continued for 4 hours at 60° C., after which the resulting crystal slurry is brought into solution by adding 600 parts of ice. This solution is stirred into 2000 parts of 12.5% strength sodium hydroxide solution, and acidified with hydrochloric acid after 6 hours. The precipitated product is filtered off under suction, washed with water and dried to give 201 parts of 2- acetylamino-3-cyano-4-ethoxy-5-formylthiophene. A sample recrystallized from dimethylformamide has a melting point of 276°-277° C. and possesses the following analytical values:

| | C₁₀H₁₀N₂O₃S (238) | | | | |
|---|---|---|---|---|---|
| calculated: | C 50.4 | H 4.2 | N 11.8 | O 20.1 | S 13.5 |
| found: | 50.5 | 4.3 | 11.9 | 20.4 | 13.2 |

Example 30

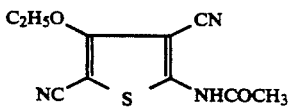

A mixture of 1000 parts of dimethylformamide, 1000 parts of water, 100 parts of hydroxylammonium chloride, 100 parts of sodium acetate and 238 parts of the compound obtained as described in Example 29 is stirred for 6 hours at 100° C. After cooling, the mixture is diluted with a further 1000 parts of water, and the product is filtered off under suction and dried at 100° C. The dry product in 900 parts of acetic anhydride is refluxed for 4 hours, and the acetic anhydride is then decomposed by the drop-wise addition of 60 parts of water. After the mixture has cooled, the product is filtered off under suction, washed with water and dried. 188 parts of 2-acetylamino-3,5-dicyano-4-ethoxythiophene are obtained in the form of grayish crystals. A sample recrystallized from dimethylformamide has a melting point of 267°-268° C. and gives the following analysis:

| | C₁₀H₉N₃O₂S (235) | | | | |
|---|---|---|---|---|---|
| calculated: | C 51.1 | H 3.8 | N 17.9 | O 13.6 | S 13.6 |
| found: | 51.0 | 3.7 | 17.6 | 14.0 | 13.4 |

Example 31

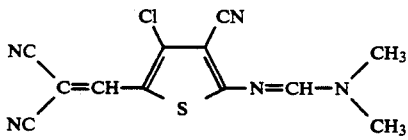

54.3 parts of N,N-dimethyl-N'-(4-chloro-3-cyano-5-formylthien-2yl)-formamidine, 14.9 parts of malonodinitrile, 1 part of 5-alanine and 200 parts of dimethylformamide are heated for 1 hour at 100° C. After the mixture has cooled to room temperature, the precipitated orange product is filtered off under suction, washed with dimethylformamide and then with water and dried. 50 parts (77% of theory) of a golden yellow compound of the above constitution are obtained.

Mp.: 257° C. (from dimethylformamide); IR (KBr): 2230, 2218 (C≡N), 1625, 1569 cm⁻¹ (C=C, C=N).

λ$_{max}$(CH₂Cl₂): 458 nm, ε: 40 800

| | C₁₂H₈ClN₅S (289.5) | | | | |
|---|---|---|---|---|---|
| calculated: | C 49.7 | H 2.8 | Cl 12.3 | N 24.2 | S 11.1 |
| found: | 49.6 | 2.7 | 12.4 | 24.2 | 11.0 |

Example 32

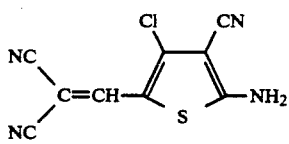

56 parts of 2-amino-4-chloro-3-cyano-5-formylthiophene, 19.8 parts of malonodinitrile, 1 part of β-alanine and 200 parts of dimethylformamide are heated for 3 hours at 100° C., after which the reaction mixture is poured onto ice water. The yellow precipitate is filtered off under suction, washed with water and dried. 65.3 parts (93% of theory) of the above compound are obtained.

Mp.:>300° C.

Example 33

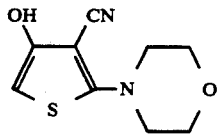

26 parts of chloroacetyl chloride and 39.1 parts of cyanoacetic acid thiomorpholide in 140 parts of dimethylformamide are initially taken, and 46.5 parts of triethylamine are added dropwise while cooling with ice. Stirring is carried out for 1 hour at room temperature, after which the solution is poured onto water to precipitate the product, and the precipitate is filtered off under suction, washed with water and dried. 30 parts (62% of theory) of 3-cyano-4-hydroxy-2-morpholinothiophene are obtained.

Mp.: 191° C. (from glacial acetic acid); IR (KBr): 2204 (C≡N), 1649 (C=O), 1562 cm⁻¹ (C=C).

| | C₉H₁₀N₂O₂S (210) | | | | |
|---|---|---|---|---|---|
| calculated: | C 51.4 | H 4.8 | N 13.3 | O 15.2 | S 15.3 |
| found: | 51.6 | 4.9 | 13.3 | 15.3 | 15.1 |

Example 34

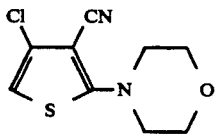

77 parts of phosphoryl trichloride are added dropwise to a mixture of 10.5 parts of 3-cyano-4-hydroxy-2-morpholinothiophene, 5.1 parts of triethylamine and 50 parts of tetrahydrofuran, and the mixture is then heated at the boil for 1 hour. The mixture is then poured onto water to precipitate the product, and the precipitate is filtered off under suction, washed with water and dried. 9.7 parts (85% of theory) of 4-chloro-3-cyano-2-morpho(inothiophene are obtained.

Mp.: 128° C. (from isopropanol); IR (KBr): 3109 (CH), 2212 cm⁻¹ (C≡N).

| C9H9ClN2OS (228.5) | | | | | |
|---|---|---|---|---|---|
| calculated: C 47.3 | H 4.0 | Cl 15.5 | N 12.3 | O 7.0 | S 14.0 |
| 47.0 | 4.0 | 15.3 | 12.0 | 7.4 | 13.9 |

| C9H10ClN3S (227.5) | | | | |
|---|---|---|---|---|
| calculated: C 47.5 | H 4.4 | Cl 15.6 | N 18.5 | S 14.1 |
| found: 47.5 | 4.4 | 15.7 | 18.4 | 14.0 |

Example 35

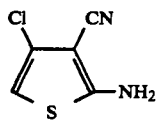

15.3 parts of phosphoryl trichloride are added to a mixture of 14 parts of 2-amino-3-cyano-4-hydroxythiophene, 7.9 parts of pyridine and 70 parts of tetrahydrofuran, and the mixture is then heated at the boil for 1 hour. After cooling, the mixture is poured onto water and left to stand overnight, and the precipitate is filtered off under suction, washed with water and dried. 9.4 parts (60% of theory) of 2-amino-4-chloro-3-cyanothiophene are obtained.

Mp.: 230° C. (from glacial acetic acid); IR (KBr): 3418, 3329, 3210, (NH2), 3118 (CH), 2215 (C≡N), 1627 cm$^{-1}$.

| C5H3ClN2S (158.5) | | | | |
|---|---|---|---|---|
| calculated: C 37.9 | H 1.9 | Cl 22.4 | N 17.7 | S 20.2 |
| found: 37.9 | 1.8 | 22.1 | 17.2 | 20.8 |

Example 36

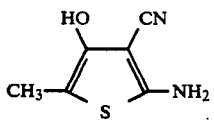

The compound is prepared as described in Example 4, except that α-chloropropionyl chloride is used instead of chloroacetyl chloride. 2-Amino-3-cyano-4-hydroxy-5-methylthiophene is obtained in 50% yield. According to the melting point and IR spectra, this compound is identical to that prepared as described in Example 3.

Example 37

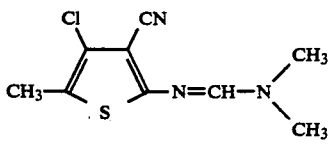

14 parts (77% of theory) of N,N-dimethyl-N'-(4-chloro-3-cyano-5-methylthien-2-yl)-formamidine are obtained from 15 parts of phosphoryl trichloride, 100 parts of dimethylformamide and 12.3 parts of 2-amino-3-cyano-4-hydroxy-5-methylthiophene, as described in Example 16.

Mp.: 84° C.; IR (KBr): 2216 (C≡N), 1622 cm$^{-1}$ (c=N).

Example 38

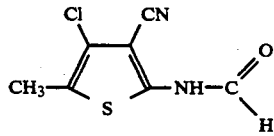

6.8 parts of N,N-dimethyl-N'-(4-chloro-3-cyano-5-methylthien-2-yl)-formamidine, 30 parts of formic acid and 30 parts of water are heated at the boil for 1 hour, and the precipitated product is filtered off under suction when the mixture is cooled, and washed with water and dried. 5.6 parts (93% of theory) of N-(4-chloro-3-cyano-5-methylthien-2-yl)-formamide are obtained.

Mp.: 258° C.; IR (KBr): 3170 (NH), 2224 (C≡N), 1685, 1644, 1580 cm$^{-1}$ (C=O).

| C7H5ClN2OS (200.5) | | | | | |
|---|---|---|---|---|---|
| calculated: C 41.9 | H 2.5 | Cl 17.7 | N 14.0 | O 8.0 | S 16.0 |
| found: 42.0 | 2.6 | 17.8 | 13.9 | 8.4 | 15.8 |

Example 39

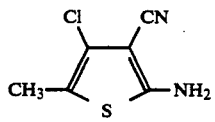

A mixture of 6.1 parts of N,N-dimethyl-N'-(4-chloro-3-cyano-5-methylthien-2-yl)-formamidine, 50 parts of ethanol and 2 parts of concentrated hydrochloric acid is heated at the boil for 1 hour. Thereafter, the mixture is added to a dilute aqueous sodium acetate solution, and the precipitate is filtered off under suction and dried. 4 parts (86% of theory) of 2-amino-4-chloro-3-cyano-5-methylthiophene are obtained.

Mp.: 158° C.; IR (KBr): 3420, 3323 (—NH2), 2214 cm$^{-1}$ (C≡N).

| C6H5ClNS (172.5) | | | | |
|---|---|---|---|---|
| calculated: C 41.7 | H 2.9 | Cl 20.5 | N 16.2 | S 18.6 |
| found: 42.0 | 3.1 | 20.0 | 16.4 | 18.0 |

Example 40

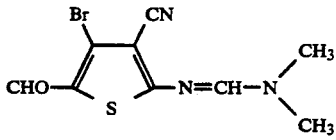

400 parts of phosphoryl tribromide are added to 700 parts of dimethylformamide while cooling with ice, the mixture is stirred for a further 0.5 hour at 5°–10° C. and 78 parts of 2-amino-3-cyano-4-hydroxythiophene are then introduced. The solution is stirred for a further hour at 70° C., after which it is poured into 2000 parts of ice water. The precipitate is filtered off under suction, washed with water and dried. 94 parts (59% of theory) of N,N-dimethyl-N'-(4-bromo-3-cyano-5-formylthien-2-yl)-formamidine are obtained.

Mp.: 220° C. (from glacial acetic acid); IR (KBr): 2222 (C≡N), 1620 cm$^{-1}$ (C=O).

| $C_9H_8BrN_3OS$ | | | | | | |
|---|---|---|---|---|---|---|
| calculated: | C 37.8 | H 2.8 | Br 27.9 | N 14.7 | O 5.6 | S 11.2 |
| found: | 37.9 | 3.3 | 27.5 | 14.6 | 6.0 | 11.1 |

Example 41

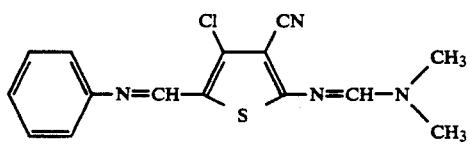

A mixture of 12.1 parts of N,N-dimethyl-N'-(4-chloro-3-cyano-5-formylthien-2-yl)-formamidine, 9.3 parts of aniline and 100 parts of methylglycol is heated at the boil for 1 hour, after which the precipitate is filtered off under suction when the mixture is cooled, and is washed with methylglycol and then with water and dried.

11.9 parts (75% of theory) of N,N-dimethyl-N'-(4-chloro-3-cyano-5-phenyliminomethylthien-2-yl)-formamidine are obtained.

Mp.: 174° C. (from methylglycol); IR (KBr): 2220 (C≡N), 1634 cm$^{-1}$ (C=N).

| $C_{15}H_{13}ClN_4S$ (316.5) | | | | | |
|---|---|---|---|---|---|
| calculated: | C 56.9 | H 4.1 | Cl 11.2 | N 17.7 | S 10.1 |
| found: | 56.8 | 4.1 | 11.2 | 17.4 | 10.0 |

Example 42

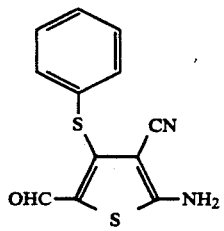

18.7 parts of 2-amino-4-chloro-3-cyano-5-formylthiophene are added to a solution of 11 parts of thiophenol, 5.4 parts of a 30% strength methanolic sodium methylate solution and 100 parts of methanol. The mixture is heated at the boil for 0.5 hour, after which it is allowed to cool and the precipitated product is filtered off under suction, washed with methanol, and then with water and dried. 21 parts (81% of theory) of 2-amino-3-cyano-5-formyl-4-phenylthiothiophene are obtained.

Mp.: 230° C. (from glacial acetic acid); IR (KBr): 3360, 3292, 3142 (NH$_2$), 2220 (C≡N), 1643, 1621, 1588 cm$^{-1}$ (C=O, C=C).

| $C_{12}H_8N_2OS_2$ (260) | | | | | |
|---|---|---|---|---|---|
| calculated: | C 55.4 | H 3.1 | N 10.8 | O 6.2 | S 24.6 |
| found: | 55.3 | 3.2 | 10.7 | 6.6 | 24.0 |

Example 43

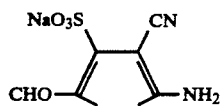

93.3 parts of 2-amino-4-chloro-3-cyano-5-formylthiophene, 126 parts of sodium sulfite and 300 parts of water are heated at the boil for 2 hours, after which 200 parts of concentrated hydrochloric acid are added to the ice-cooled mixture, and the mixture is left to stand overnight. Thereafter, the mixture is filtered under suction, and the residue is washed with a little ice water and dried. 85 parts (67% of theory) of sodium 2-amino-3-cyano-5-formylthien-4-ylsulfonate are obtained.

Mp.:>300° C.; IR (KBr): 3385, 3303, 3191 (NH$_2$), 2233 (C≡N), 1608 cm$^{-1}$ (C=O).

| $C_6H_3N_2NaO_4S$ (254) | | | | | | |
|---|---|---|---|---|---|---|
| calculated: | C 28.4 | H 1.2 | N 11.0 | Na 9.1 | O 25.2 | S 25.2 |
| found: | 28.3 | 1.2 | 10.9 | 8.7 | 25.7 | 24.7 |

Example 44

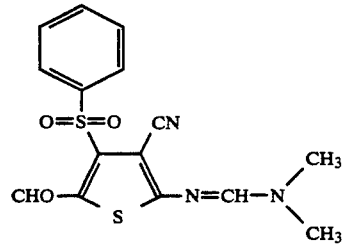

A mixture of 12.1 parts of N,N-dimethyl-N'-(4-chloro-3-cyano-5-formylthien-2-yl)-formamidine, 8.2 parts of sodium phenylsulfinate and 70 parts of methylglycol is heated at the boil for 1 hour. The precipitated product is then filtered off under suction when the mixture is cold and is washed with methylglycol and then with water and dried. 9.7 parts of N,N-dimethyl-N'-(3-cyano-5-formyl-4-phenylsulfonylthien-2-yl)-formamidine are obtained.

Mp.: 262° C.; IR (KBr): 2225 (C≡N), 1649, 1622 cm$^{-1}$ (C=N, C=O).

| $C_{15}H_{13}N_3O_3S$ (347) | | | | | |
|---|---|---|---|---|---|
| calculated: | C 51.9 | H 3.8 | N 12.1 | O 13.8 | S 18.5 |
| found: | 52.0 | 3.9 | 12.1 | 14.0 | 18.5 |

Example 45

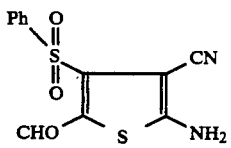

A solution of 82 parts of sodium phenylsulfinate in 500 parts of water is added to a mixture of 93.3 g of 2-amino-4-chloro-3-cyano-5-formylthiophene an 500 parts of methylglycol, and the reaction mixture is heated at the boil for 6 hours. Thereafter, the solution is filtered while hot and the filtrate is left to stand overnight. The precipitated product is then filtered off under suction, washed with water and dried. 121 parts (83% of theory) of 2-amino-3-cyano-5-formyl-4-phenyl-sulfonylthiophene are obtained.

Decomposition temperature: 230° C. (from glacial acetic acid); IR (KBr): 3316, 3217 (NH$_2$), 2220 (CN), 1648, 1626, 1609 cm$^{-1}$.

The novel compounds of the formula

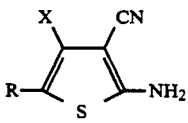

are useful diazo components and can be diazotized, for example, in a glacial acetic acid/propionic acid mixture or in sulfuric acid with nitrosylsulfic acid, and the product then reacted with coupling components.

EXAMPLE 46

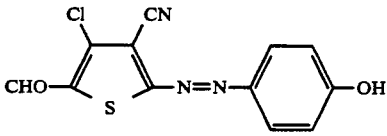

9.3 parts of 2-amino-4-chloro-3-cyano-5-formylthiophene are dissolved in 60 parts of concentrated sulfuric acid at no higher than 20° C., after which 16.6 parts of nitrosylsulfuric acid (11.5% of N$_2$O$_3$) are added dropwise to the solution at 0°–5° C. Stirring is continued for a further 4 hours at 0°–5° C., and the resulting diazonium salt solution is run slowly, at 0° C., into a mixture of 4.7 parts of phenol, 3 parts of sodium hydroxide, 0.5 part of amidosulfonic acid, 200 parts of water and 400 parts of ice. When coupling is complete, the dye is washed neutral and dried. 12.2 parts (84% of theory) of the yellow dye of the above formula are obtained. $\lambda_{max}$(CH$_2$Cl$_2$): 438 nm, $\epsilon$: 24200.

We claim:

1. A thiophene derivative of the formula

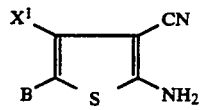

wherein X$^1$ is chlorine, methoxy, ethoxy, phenylthio, methylsulfonyl or phenylsulfonyl and B is formyl.

2. A thiophene derivative of the formula

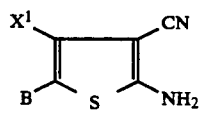

wherein X$^1$ is chlorine, methoxy, ethoxy, phenylthio, methylsulfonyl or phenylsulfonyl and B is hydroxysulfonyl.

3. A thiophene derivative of the formula

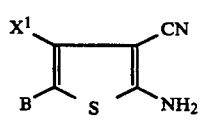

wherein X$^1$ is chlorine, methoxy, ethoxy, phenylthio, methylsulfonyl or phenylsulfonyl and B is a radical of the formula CH=T, where T is

and Z is hydrogen, cyano, carboxyl, and carboxylic ester group, unsubstituted or substituted carbamyl, benzimidazolyl, benzoxazolyl or benzothioazolyl.

* * * * *

UNITED STATES PATENT AND TRADEMARK OFFICE
CERTIFICATE OF CORRECTION

PATENT NO. : 5,206,375
DATED : April 27, 1993
INVENTOR(S) : Ernst Schefczik et al It is certified that error appears in the above-indentified patent and that said Letters Patent is hereby corrected as shown below:

On the title page, Item [63],

The Related U.S. Application Data is incorrect, should read:

--Continuation of Ser. No. 512,583, Apr. 23, 1990, abandoned, which is a continuation of Ser. No. 385,951, Jul. 28, 1989, abandoned, which is a continuation of Ser. No. 282,856, Dec. 9, 1988, abandoned, which is a continuation of Ser. No. 833,281, Feb. 27, 1986, abandoned--

Signed and Sealed this

Twelfth Day of April, 1994

*Attest:*

BRUCE LEHMAN

*Attesting Officer*         *Commissioner of Patents and Trademarks*